United States Patent [19]

Hall et al.

[11] Patent Number: 5,266,609
[45] Date of Patent: Nov. 30, 1993

[54] DENTAL RESTORATIVE ADHESIVE HAVING IMPROVED FRACTURE TOUGHNESS

[76] Inventors: Neil R. Hall, 14 Kintore Street, Wahroonga, New South Wales 2076; Christopher P. Doube, 130 Middleharbour Road, Lindfield, New South Wales 2070, both of Australia

[21] Appl. No.: 914,655

[22] Filed: Jul. 17, 1992

Related U.S. Application Data

[63] Continuation of Ser. No. 602,282, filed as PCT/AU90/00023, Jan. 25, 1990, published as WO90/08799, Aug. 9, 1990, abandoned.

[30] Foreign Application Priority Data

Jan. 27, 1989 [AU] Australia .................. PJ2437

[51] Int. Cl.$^5$ ........................ A61K 6/09; C08K 3/34
[52] U.S. Cl. .................... 523/116; 524/445; 524/449; 524/451; 524/492; 524/493; 524/494
[58] Field of Search .................. 106/35; 523/116, 413; 524/436, 439, 440, 441, 442, 447, 448, 449, 451, 492, 493, 494, 495, 496, 514, 847

[56] References Cited

U.S. PATENT DOCUMENTS

| | | | |
|---|---|---|---|
| 2,938,011 | 5/1960 | Wormuth | 523/220 |
| 3,158,528 | 11/1964 | Brown | 523/220 |
| 3,452,437 | 7/1969 | Chang | 523/116 |
| 4,100,122 | 7/1978 | Kent | 524/494 |
| 4,107,845 | 8/1978 | Lee, Jr. et al. | 523/116 |
| 4,239,113 | 12/1980 | Gross et al. | 523/220 |
| 4,297,266 | 10/1981 | Ibsen et al. | 523/116 |
| 4,389,497 | 6/1983 | Schmitt et al. | 523/116 |
| 4,407,984 | 10/1983 | Ratcliffe et al. | 523/116 |
| 4,649,165 | 3/1987 | Kuhlmann | 523/116 |

FOREIGN PATENT DOCUMENTS

| | | | |
|---|---|---|---|
| 1171560 | 4/1964 | Fed. Rep. of Germany | 106/35 |
| 0118009 | 9/1981 | Japan | 106/35 |

*Primary Examiner*—Paul R. Michl
*Assistant Examiner*—Peter Szekely
*Attorney, Agent, or Firm*—Lowe, Price, LeBlanc & Becker

[57] ABSTRACT

The invention relates to an improved, castable, synthetic resin material, suitable for use in dental and medical restorations, as a replacement for dental enamel and hydroxyapatite bone material. This material is also useful for electrical insulation. More specifically, the invention provides a filled reinforced resin matrix comprising a castable resin; from 5 to 50% vol of fibers of 50 μm or less diameter; from 10 to 35% vol of a first particulate filler having a particle size range of 0.1 to 50 μm; and from 5 to 25% vol of a second particulate filler having an ultimate particle size range of 10 to 100 nm.

21 Claims, No Drawings

DENTAL RESTORATIVE ADHESIVE HAVING IMPROVED FRACTURE TOUGHNESS

No. 07/602,282 filed as PCT/AU90/00023, Jan. 25, 1990, published as WO90/08799, Aug. 9, 1990, now abandoned.

TECHNICAL FIELD

The invention relates to an improved, castable, synthetic resin material, suitable for use in dental and medical restorations, as a replacement for dental enamel and hydroxyapatite bone material. This material is also useful for electrical insulation.

BACKGROUND ART

Castable, synthetic resin materials currently on the market are perceived to be brittle in performance, particularly when they are compared with metals that have been traditionally used in dental and medical restorative applications. However, metal systems such as alloys and amalgams suffer from limited biocompatability and high heat and electrical conductivity, these deficiencies having negative health implications.

Dental composite resins have been developed from castable, synthetic resins especially for dental applications. Dental composite resins are characterized by extensive variation in the resin matrices utilized, ranging from acrylic through epoxy to recently developed urethane modified resins. Dental composite resin materials are easy to use and polish, they are photocurable and/or chemically curable and are relatively tough, strong and durable.

Dental composite resin materials are different from most castable, synthetic resin materials in that they are highly loaded (up to 90% and possibly further) with fine filler particles, and are predominantly photocured.

In general, dental composite resin materials include synthetic resins such as bis/GMA, urethane dimethacrylates, difunctional monomers such as TEDGMA; photoinitiators; amine accelerators; and polymerisation inhibitors and reinforcing fillers such as precipitated and pyrogenic silica, fine particles of glass (Ba, B, Sr, Al, Li, —$SiO_2$) silica (quartz) or ceramic. Dental composite resins are classified as conventional, microfine or hybrid depending on the reinforcing fillers used.

A typical hybrid formula is 15% bis/GMA, 15% TEDGMA, 50% pyrogenic silica, 20% Ba glass and <1% photoinitiators.

Biocompatibility is still being investigated, however, dental composite resins appear to be more biocompatible than metals.

The filler particles used are generally small (<5 µm) so as to enable greater filler loadings and enhance physical properties such as polymerisation shrinkage, plain strain fracture toughness ($K_{1c}$) surface polishability and retained smoothness. Conventional dental composite resins with larger particles (<30 µm) cause unacceptable surface roughness of restorations (fillings) when the inevitable surface wear of the matrix resin occurs.

Existing dental composite resins do not have the necessary physical properties to be universally endorsed as amalgam replacements.

The current invention relates to the finding that the strength and toughness of castable, synthetic resinMs can be further improved by the incorporation of fibres or platelets or combinations thereof.

Particles can be defined as having similar extent in three dimensions whereas fibres have substantially greater extent in one dimension compared to two dimensions, and platelets have substantially greater extent in two dimensions compared to one dimension.

In particular, the strength and toughness of dental composite resins and their acceptability as amalgam replacements can be improved without substantially reducing the acceptability of the dental composite resin for curing and surface finishing, by the incorporation of fibres, platelets or combinations thereof. Fibres and platelets produce greater $K_{1c}$ than particles because of the higher energy required for debonding fibres or platelets compared to particles from a resin matrix. Hence more energy is required for fracture to occur.

Fibre reinforcement of castable, synthetic resins has been investigated [Krause et al "Mechanical properties of BIS-GMA resin short glass fiber composites", J. Biomed Materials Res. 23, 1195-1121 (1989)]. The authors of this paper were not able to demonstrate that improved strengths could be achieved in resins reinforced with fibres alone.

DESCRIPTION OF THE INVENTION

Surprisingly, it has been found that castable, synthetic resins with a particular combination of particulate and fibre reinforcement have improved strengths and fracture toughness over conventional castable, synthetic resins and over castable, synthetic resins reinforced with fibres alone. The new castable, synthetic resins of the invention, because of their improved mechanical properties have wider application than conventional castable, synthetic resins.

The invention provides a filled reinforced resin matrix comprising a castable resin; from 5 to 50% vol., preferably 25 to 35%, of fibres of 50 µm or less diameter, preferably 10 to 20 µm diameter; from 10 to 65% vol, preferably 40-50%, of a first particulate filler having a particle size range of 0.1 to 50 µm and a preferred average size of less than 5 µm; and from 5 to 25% vol, preferably 10 to 20%, of a second particulate filler having an ultimate particle size range of 10 to 100 nm, preferably approximately 40 nm, and preferably a surface area of 50 $m^2g^{-1}$ or less.

By ultimate particle size we mean the particle size which is present in the matrix and may include agglomerates of the second particulate filler.

Suitable resins include acrylates, epoxies and urethanes. Examples of such resins are diglycidyl ether of bisphenol-A-dimethacrylate, ethylene glycol dimethacrylate or triethylene glycol dimethacrylate (hereinafter referred to as Bis/GMA, EGDMA and TEGDMA respectively). Further examples of such resins include oligo dimethacrylates, oligo glycol dimethacrylates, oligo bisphenol A dimethacrylates, urethane dimethacrylates and urethane methacrylates.

A variety of fibre types can be utilised such as borosilicate ("E" glass) fibres, silica fibres, ceramic fibres, metal fibres and polymeric fibres. Long fibres (glass or carbon/graphite) can be used for fixed prosthodonture or implants. Very short fibres and platelets are particularly suitable for tooth restorations. The fibres can be mixed with the resins in a vacuum mixer to eliminate trapped air. For dental composite resins the fibres can be incorporated with the other particulate fillers and mixed with the resins in a vacuum mixer to eliminate trapped air.

For dental composite resins, the fibres preferably have an aspect (length:diameter) ratio of 50:1. Fibre length would generally be 5 µm to 2.5 mm, preferably 5

μm to 1 mm and more preferably 50 to 500 μm. For a diameter of 5 to 50 μm the length would be 0.25 to 2.5 mm for dental composite resins, unless the resins were to be used to manufacture bridges, where longer fibres would be employed.

Fibres of all types can be added to existing dental composite resin formulae in varying concentrations, resulting in a considerable increase in $K_{1c}$ even at low concentrations such as 5%.

Fibres add substantially to the toughness and fracture resistance of the dental composite resin, due to the synergistic combination of filler particles and the fibres. An optimum is reached at approximately 30 to 50% fibre for each combination, until at high fibre concentration, 60 to 70%, the beneficial effect rapidly decreases with the corresponding decrease in other filler content.

Suitable particulate fillers include silica, porous amorphous silica (diatomaceous earth), feldspar, mica and talc.

Fillers, such as porous amorphous silica (diatomaceous earth), interlock very positively with the resin matrix, acting essentially as very short fibres, and significantly increase $K_{1c}$ over fine particles (glass, silica etc) at similar concentrations. They produce the highest $K_{1c}$ values for anterior dental composite resins where small particles are essential to allow the surface to be polished to reproduce the high gloss of natural teeth. Compared to the normal microfine anterior dental composite resins, adding fillers can increase $K_{1c}$ values by more than two times. The second particulate filler may be, e.g. pyrogenic silica or fine titania, zirconia or alumina.

Generally the reinforced dental composite resin compositions of the invention exhibit increased strength and toughness of between 200% and 400% relative to dental composite resins when this increase is measured as $K_{1c}$ in MN/m 3/2.

The compositions of the invention may be precast, polymerised in situ, or part polymerised in situ, removed and post-cured.

BEST METHODS OF CARRYING OUT THE INVENTION

Preferred composites are made up of approximately 30% vol resin, approximately 30% vol fibres, approximately 30% vol of the first particulate filler and approximately 10% vol of the second particulate filler.

The following examples illustrate preferred embodiments of the invention.

EXAMPLE 1

A reinforced resin of the following composition was prepared.

| | |
|---|---|
| Resin (12% Bis/GMA 12% TEGDMA) | 24% |
| Silica (average 17 μm) | 29% |
| Pyrogenic Silica (average 50 μm) | 9% |
| Borosil Fiber (diameter 15 μm length 400–800 μm) | 38% |

The paste is produced in small quantities by gradually introducing the premixed filler to the resin in a suitable size pestle and mortar. The added filler has to be thoroughly mixed before adding further filler in small increments. As the filler content percentage rises large shear forces are required. Preferably the paste should be placed under vacuum to eliminate trapped air in the mix.

The resultant composite can be chemically cured using a two paste system but preferably photocured as a single paste. The resin is mixed with an appropriate photoinitiator, either UV or visible light sensitive, an amine accelerator and a suitable amount of inhibitor to suit the particular application.

The resin of Example 1 has a plain strain fracture toughness ($K_{1c}$) of 1.6 MN/m$^{1.5}$.

EXAMPLE 2

A reinforced resin of the following composition was prepared.

| | |
|---|---|
| Resin (Bis/GMA/TEGDMA) | 28% |
| Silica (average 17 μm) | 27% |
| Pyrogenic Silica (average 50 μm) | 9% |
| Borosil Fiber (diameter 15 μm length 400–800 μm) | 36% |

The resin is produced in accordance with the method described in Example 1. Increasing the resin content achieves a more optimum resin wetting of the fibres and increases the $K_{1c}$ to 2.5 in the resin of this example.

EXAMPLE 3

A reinforced resin of the following composition was prepared.

| | |
|---|---|
| Resin (Bis/GMA/TEGDMA) | 29% |
| Silica (average 17 μm) | 36% |
| Pyrogenic Silica (average 50 μm) | 12% |
| Borosil Fiber (diameter 15 μm length 400–800 μm) | 23% |

The resin is produced in accordance with the method described in Example 1. This resin has a $K_{1c}$ of 1.2 MN/m$^{1.5}$.

EXAMPLE 4

A reinforced resin of the following composition was prepared.

| | |
|---|---|
| Resin (Bis/GMA/TEGDMA) | 29% |
| Silica (average 17 μm) | 24% |
| Pyrogenic Silica (average 50 μm) | 14% |
| Borosil Fibers (diameter 15 μm length 400–800 μm) | 33% |

The resin is produced in accordance with the method described in Example 1. Replacing some of the silica in the composition of Example 3 with fibre, increasing the fibre content from 23% to 33%, doubles the $K_{1c}$ to 2.8 MN/m$^{1.5}$.

INDUSTRIAL APPLICATION

The resin matrices of the invention can be used in place of amalgam in dental restorations. They can also be used as a core material in dental restorations as dental implants and as a replacement for hydroxyapatite bone repair materials. Other tooth coloured dental restorative materials such as glass ionomers and cermets (low $K_{1c}$s) would be greatly strengthened by fibres, platelets or combinations thereof.

Longer glass or carbon/graphite fibres are suitable for strengthening dental composite resins for use in dental implants and fixed prosthodonture (crowns and bridges) either precast or polymerised in situ.

Matrices according to the invention can be used to provide improved electrical insulator casting resins.

Because of the biocompatibility and mechanical properties of the materials of the invention, they also find use as bone prostheses.

We claim:

1. A dental restorative adhesive having improved fracture toughness and comprising 24 to 29 volume % of a castable dental synthetic resin selected from the group consisting of acrylate, epoxy or urethane; from 5 to 50% vol of fibres of 50 μm or less diameter; from 10 to 65% vol of a first particulate filler having a particle size range of 0.1 to 50 μm; and from 5 to 25% vol of a second particulate filler having an ultimate particle size range of 10 to 100 nm, said composite having a Kic value of at least $1.2 \text{ MN/m}^{1.5}$.

2. A composite as defined in claim 1, wherein the fibres are borosilicate (E glass) fibres, silica fibres, ceramic fibres, metal fibres, carbon fibres or polymeric fibres.

3. A composite as defined in claim 1, wherein the amount of fibres is 25 to 35% vol.

4. A composite as defined in claim 1, wherein the fibre diameter is 10 to 20 μm.

5. A composite as defined in claim 1, wherein the fibre length is 5 μm to 2.5 mm.

6. A composite as defined in claim 1, wherein the fibre length is 5 μm to 1 mm.

7. A composite as defined in claim 1, wherein the fibre length is 50 to 500 μm.

8. A composite as defined in claim 1, wherein the fibres have an aspect ratio of 50:1.

9. A composite as defined in claim 1, wherein the first particulate filler is silica, a porous amorphous silica (diatomaceous earth), feldspar, mica or talc.

10. A composite as defined in claim 1, wherein the amount of first particulate filler is 40 to 50% vol.

11. A composite as defined in claim 1, wherein the particle size range of the first particulate filler is less than 5 μm.

12. A composite as defined in claim 1, wherein the second particulate filler is pyrogenic silica or fine titania, zirconia or alumina.

13. A composite as defined in claim 1, wherein the amount of second particulate filler is 10 to 20% vol.

14. A composite as defined in claim 1, wherein the particle size of second particulate filler is approximately 40 nm.

15. A composite as defined in claim 1, wherein the surface area of the second particulate filler is 50 $m^2g^{-1}$ or less.

16. A composite as defined in claim 1, wherein the resin is an oligo dimethacrylate, an oligo glycol dimethacrylate, an oligo bisphenol A dimethacrylate, a urethane dimethacrylate or a urethane methacrylate.

17. A composite as defined in claim 16 wherein the resin is di-glycidyl ether of bisphenol-A-dimethacrylate, ethylene glycol dimethacrylate or triethylene glycol dimethacrylate.

18. A dental restorative composite having improved strength and fracture toughness in dental restorations and comprising approximately 30% vol of a castable dental synthetic resin selected from the group consisting of acrylate, epoxy or urethane; approximately 30% vol of fibres of 50 μm or less diameter; approximately 30% vol of a first particulate filler having a particle size range of 0.1 to 50 μm; and approximately 10% vol of a second particulate filler having an ultimate particle size range of 10 to 100 nm.

19. A method for restoring a tooth which comprises applying a composite of claim 1 to the tooth and curing the composite.

20. A method according to claim 19, wherein the composite is applied to the tooth as a core material or as a dental implant.

21. A method according to claim 19, wherein curing is by photocuring.

* * * * *